United States Patent [19]
Kroll et al.

[11] Patent Number: 5,643,323
[45] Date of Patent: Jul. 1, 1997

[54] SYSTEM AND METHOD INDUCING FIBRILLATION USING AN IMPLANTABLE DEFIBRILLATOR

[75] Inventors: Mark W. Kroll, Minnetonka; James E. Brewer, Maplewood, both of Minn.

[73] Assignee: Angeion Corporation, Plymouth, Minn.

[21] Appl. No.: 486,761

[22] Filed: Jun. 7, 1995

[51] Int. Cl.⁶ .................................................. A61N 1/362
[52] U.S. Cl. .................................................. 607/2
[58] Field of Search .......................... 607/2, 5, 75, 76; 128/697

[56] References Cited

U.S. PATENT DOCUMENTS 3,602,229  8/1971  Jaros et al. .
4,705,043  11/1987  Imran .
5,129,392  7/1992  Bardy et al. .
5,279,293  1/1994  Anderson et al. .

FOREIGN PATENT DOCUMENTS 0460324   1/1990  European Pat. Off. .
0589252A2 1/1993  European Pat. Off. .

Primary Examiner—William E. Kamm

[57] ABSTRACT

A method and apparatus for inducing fibrillation generates a continuous fibrillation waveform from the internal battery source of an implantable cardioverter defibrillator. The continuous fibrillation waveform has a voltage of at least 5 volts and not more than 50 volts and a duration of not less than 500 milliseconds and is applied though the at least two implantable electrodes so as to induce fibrillation in the heart of the human patient.

29 Claims, 5 Drawing Sheets

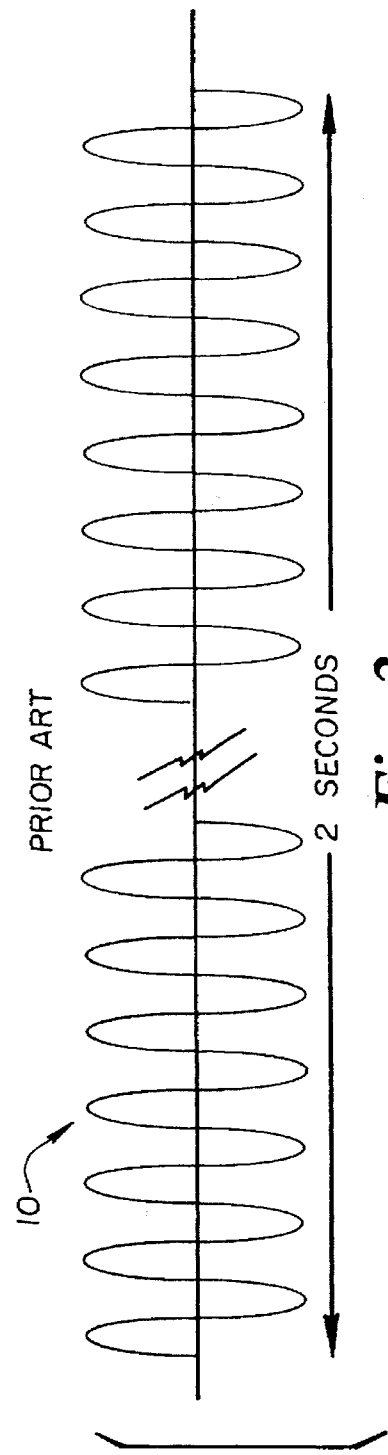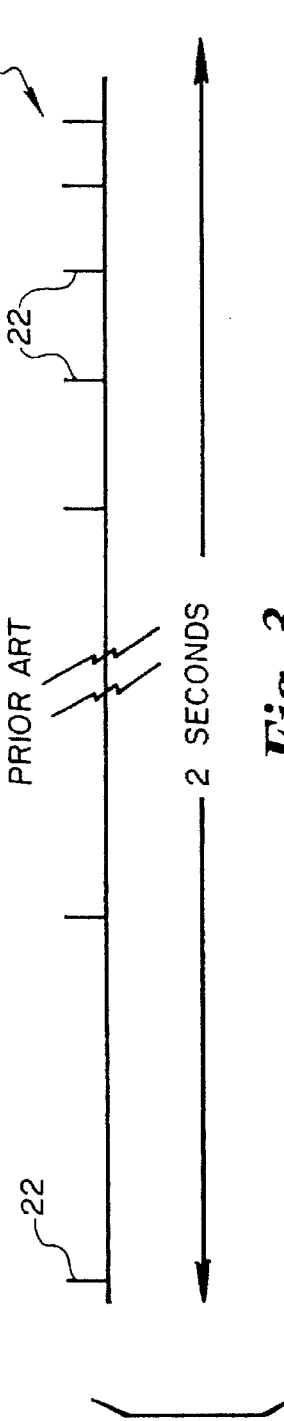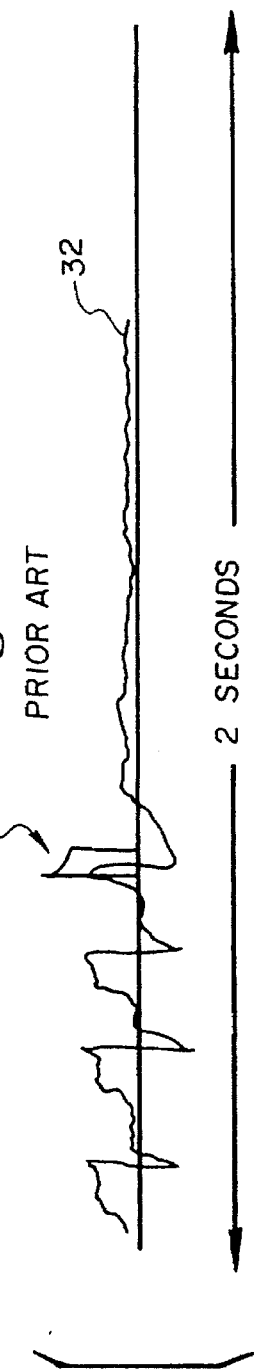

2 SECONDS

2 SECONDS

5 SECONDS

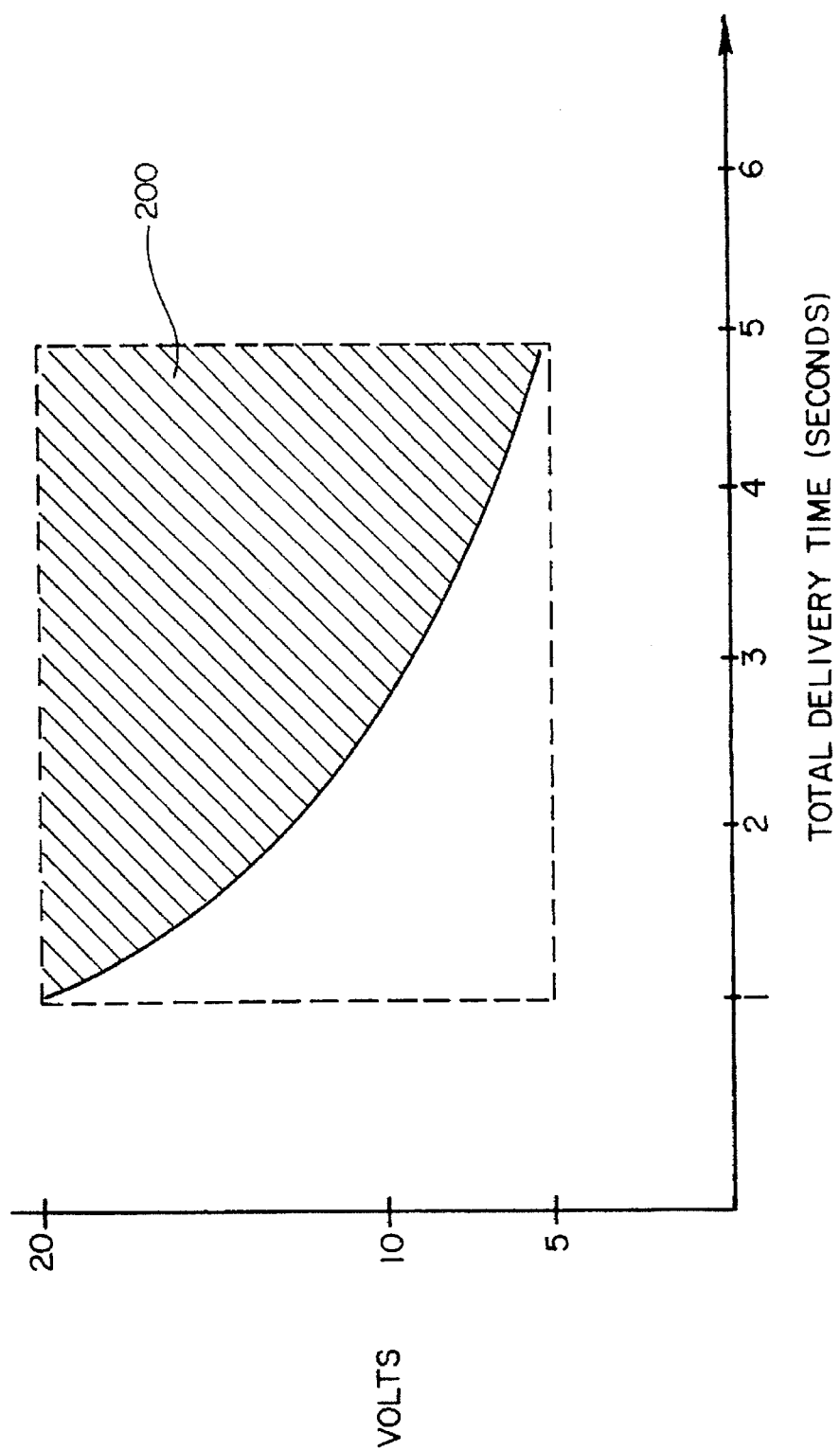

SYSTEM AND METHOD INDUCING FIBRILLATION USING AN IMPLANTABLE DEFIBRILLATOR

FIELD OF THE INVENTION

The present invention relates generally to implantable defibrillators. More particularly, the present invention relates to a method and apparatus for inducing fibrillation in a human patient using a continuous fibrillation waveform generated by the implantable defibrillator.

BACKGROUND OF THE INVENTION

As part of the medical procedure for implanting an implantable defibrillator within a human patient, it is necessary to determine a defibrillation threshold (DFT) that will be effective for that particular patient. The DFT establishes a minimum value for the initial defibrillation countershock which is to be delivered by the implantable defibrillator in the event of a cardiac arrhythmia. A preferred procedure for establishing a DFT during the implantation of an implantable defibrillator is to induce a fibrillation in the patient's heart (i.e., causing the patient's heart to stop pumping), and then using the implantable defibrillator to deliver a defibrillation countershock of a given energy value in an attempt to defibrillate the heart. If defibrillation at the given value is not successful, a very high energy defibrillation countershock is applied from an external defibrillator in order to resuscitate the patient. This procedure is repeated using increasing values for the defibrillation countershock until the defibrillation countershock delivered by the implantable defibrillator is successful in resuscitating the patient, or until the maximum energy value of the implantable defibrillator is exceeded.

In order to conduct this type of DFT test procedure, it is necessary to induce a fibrillation of the patient's heart. Numerous techniques are known for inducing fibrillation by electrical, chemical or other means. During early implantation procedures for implantable defibrillation, it was common for the implantation procedure to involve a transthoracic operation where the heart was exposed so as to allow defibrillation electrodes, such as patch electrodes, to be secured to the heart. In this type of transthoracic operation, it was relatively simple to induce fibrillation of the heart by applying, for example, a 60 Hertz alternating current (AC) signal directly to the exposed heart. As procedures have evolved for the non-transthoracic implantation of implantable defibrillators, the use of externally applied electrical signals to induce fibrillation have become more complicated and less attractive. Accordingly, techniques have been developed to induce fibrillation using the circuitry and implantable leads of the implantable defibrillator system.

The most common technique for inducing fibrillation using an implantable defibrillator is to overdrive a series of pacing pulses applied to the heart so as to induce fibrillation. An example of this overdrive power technique is described in U.S. Pat. No. 4,705,043. In this technique, the patient's heart rate is established and a set of overdrive pacing pulses are then delivered through the implantable pacing electrodes at a rate faster than the patient's heart rate, hence the term "overdrive". While this technique avoids the problems of trying to incorporate a traditional 60 Hertz AC fibrillation signal within an implantable defibrillator, this technique takes longer to induce fibrillation than the traditional 60 Hertz technique and sometimes fails to successfully induce fibrillation. As a result, the patient's heart is subjected to additional stress than would have otherwise been required for induction of fibrillation using 60 Hertz AC techniques, and the implantation procedure is more complicated when this technique fails to induce fibrillation.

Another technique uses a fibrillation-inducing waveform consisting of a medium energy countershock on the order of 100 volts which is intentionally delivered into the T-waves through a pair of defibrillation electrodes. Normally, the delivery of a countershock into the T-wave is considered to be a complication of cardioversion therapy due to the high risk of inducing fibrillation in this situation. In this technique, however, the "complication" is intentionally utilized for the purpose of intentionally inducing fibrillation in order to test the implantable defibrillator. One example of this type of shock into the T-wave technique is shown in U.S. Pat. No. 5,129,392 issued to Bardy, et al. As with the overdrive pacing technique, the shock into the T-wave technique is not completely reliable. In addition, a countershock of this nature is quite painful in the event the patient is not under anesthesia. Also, because the T-wave is a rather subtle and poorly defined characteristic of an electrocardiogram signal, it is sometimes difficult to use the T-wave to produce the accurate synchronization necessary for consistent induction of fibrillation.

Another technique for inducing fibrillation using an implantable defibrillator is disclosed in European Patent Application EP 0 589 252 82, which describes a technique for generating a multiphasic fibrillation-inducing pulse train as applied to the defibrillation electrodes. The fibrillation-inducing pulse train consists of a series of pulses having a nominal voltage on the order of 15 volts and a pulse width of preferably 1.1 milliseconds with a delay between successive pulses that ranges from 30 to 50 milliseconds. The fibrillation-inducing pulse train is generated by first charging the high voltage capacitor which also delivers the defibrillation countershock to a voltage equal to the nominal voltage and then using additional circuitry and switches separate from the circuitry and switches associated with the delivery of a defibrillation countershock to deliver the fibrillation-inducing pulse train. While this technique may have advantages over the overdrive pacing technique in that fibrillation may be induced more quickly and more consistently, this technique has the disadvantage in that it requires additional circuitry not normally associated with the implantable defibrillator. In addition, the fibrillation which is typically induced using this technique tends to be a relative coarse fibrillation wherein the electrical activity of the heart, even though in fibrillation, still exhibits a relatively high degree of organization and coordination. As such, this type of coarse fibrillation does not provide for an optimal test of the DFT of the implantable defibrillator.

While it is desirable to provide for a system for inducing fibrillation that is part of the implantable defibrillator, the present techniques for inducing fibrillation using an implantable defibrillator are not as effective as the traditional technique of applying an external 60 Hertz AC signal to the exposed heart. Accordingly, it would be advantageous to provide a system for inducing fibrillation using an implantable defibrillator which improved upon the effectiveness of the current techniques without requiring that significant additional circuitry be included within the implantable defibrillator.

SUMMARY OF THE INVENTION

The present invention provides a method and apparatus for inducing fibrillation by generating a continuous fibrillation waveform from the internal battery source of an implantable cardioverter defibrillator. The continuous fibrillation waveform has a voltage of at least 5 volts and not more than 50 volts and a duration of not less than 500 milliseconds and is applied though the at least two implantable electrodes so as to induce fibrillation in the heart of the human patient.

In accordance with a first aspect of the present invention, a method of operating an implantable defibrillator device to induce fibrillation in a heart of a human patient. The implantable defibrillator device comprising at least two human implantable electrodes and a self-contained human implantable housing containing a battery system, a transformer system, a capacitor system and a control system for selectively charging the capacitor system to a voltage greater than 50 volts using the battery system and the transformer system and selectively discharging the capacitor system in response to a cardiac dysrhythmia in the human patient through the at least two implantable electrodes as a defibrillation waveform. The method comprising the device-implemented steps of: (a) receiving a command to generate a fibrillation waveform for the purpose of testing the implantable defibrillator device; and (b) causing a continuous fibrillation waveform having a voltage of at least 5 volts and not more than 50 volts and a duration of not less than 500 milliseconds to be applied though the at least two implantable electrodes so as to induce fibrillation in the heart of the human patient.

In accordance with a second aspect of the present invention, an implantable defibrillator device is provided for inducing fibrillation in a human patient for the purpose of testing the device. The implantable defibrillator device comprises at least two human implantable electrodes and a self-contained human implantable housing. Within the housing are a battery system having a low voltage output of less than 20 volts, a transformer system electrically connected to the low voltage output of the battery system and having a high voltage output of at least 50 volts, a capacitor system electrically connected to the high voltage output of the transformer system, and control means for controlling operation of the device. The control means includes defibrillation means for selectively controlling delivery of a high voltage de fibrillation countershock from the capacitor system to the implantable electrodes; and fibrillation means for selectively controlling delivery of a continuous fibrillation waveform to the implantable electrodes, the fibrillation waveform having a voltage of at least 5 volts and not more than 50 volts and a duration of not less than 500 milliseconds.

BRIEF DESCRIPTION OF THE DRAWINGS

FIG. 1 is a graphic representation of a prior art technique of inducing fibrillation using an external 60 Hertz 110 waveform.

FIG. 2 is a graphic depiction of a prior art technique of inducing fibrillation using a series of overdrive pacing pulses.

FIG. 3 is a graphic depiction of the prior art technique of inducing fibrillation by delivering a countershock into the T-wave.

FIG. 9 is a graphic representation of another prior art technique for inducing fibrillation,

DESCRIPTION OF THE PREFERRED EMBODIMENT

Figure 4:
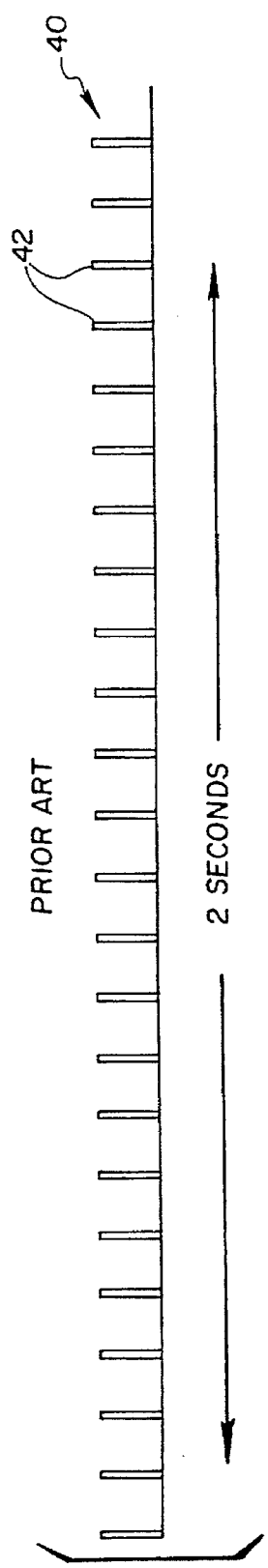
FIG. 4 is a graphic depiction of the prior art technique of inducing fibrillation using a train of pulses.

To understand the present invention it is helpful to first describe the existing techniques for inducing fibrillation as part of the implantation procedure for an implantable defibrillator. Referring to FIG. 1, a graphic representation of a 60 Hertz, 110 volt fibrillation-inducing waveform 10 is shown. This type of waveform is essentially generated by directly tapping into standard AC household current. In a transthoracic implantation procedure where the chest of the patient is opened to allow for direct access to the heart, fibrillation-inducing waveform 10 can be easily administered to the heart by placing a pair of electrodes connected to an external waveform generating apparatus (not shown) and then applying defibrillation waveform 10.

With the advent of non-transthoracic implantation procedures for implantable defibrillators, the ability to use fibrillation-inducing waveform 10 became more complicated and required the insertion of additional catheter electrodes coupled to the external waveform generating apparatus in order to supply fibrillation-inducing waveform 10 to the heart. Consequently, several prior art techniques have been developed that use the implantable defibrillator itself to generate the defibrillation-inducing waveform, thereby decreasing the complication of the implantation of the procedure. FIG. 2 shows an overdrive pacing technique for inducing fibrillation. Fibrillation-inducing waveform 20 is comprised of a series of pacing pulses 22 which are delivered through a pair of pacing electrodes. Each pacing pulse typically has a voltage output corresponding to a six volt battery system used to power the pacing circuitry associated with an implantable defibrillator. Overdrive pacing pulses begin with a broad inter-pulse spacing of, for example, 100 milliseconds, and the inter-pulse spacing is steadily decreased. An example of this technique which uses an external pacemaker to communicate a ramp pacing timing for a series of pulse drive pacing pulses 22 through telemetry to an implantable defibrillator is shown in U.S. Pat. No. 4,705,043. Unfortunately, the overdrive pacing technique for inducing defibrillation is not extremely reliable.

FIG. 3 shows another prior art technique for inducing fibrillation using an implantable defibrillator. In this technique, a fibrillation-inducing waveform 30 consists of a medium energy countershock on the order of volts which is intentionally delivered into a T-wave as detected from sensing electrodes and shown at 32. Through a pair of defibrillator electrodes. Normally, the delivery of a countershock into the T-wave 32 is considered to be a complication of cardioversion therapy due to the high risk of inducing fibrillation in this situation. In this prior art technique, however, the "complication" is utilized for the purpose of intentionally inducing fibrillation in order to test the implantable defibrillator. One example of this type of shock into the T-wave technique is shown in U.S. Pat. No. 5,129, 392 issued to Bardy, et al. As with the overdrive pacing technique, the shock into the T-wave technique is not completely reliable. In addition, a countershock of this nature is quite painful in the event the patient is not under anesthesia. Also, because the sensed T-wave 32 is a rather subtle and poorly defined characteristic of an electrocardiogram signal, it is sometimes difficult to use the T-wave to produce the accurate synchronization necessary for consistent induction of fibrillation.

In FIG. 4, another prior art technique for inducing fibrillation is shown. In this technique, a fibrillation-inducing waveform 40 consists of a train of pulses 42 which, unlike pacing pulses 22 of the overdrive pacing technique, are generated using the high voltage capacity storage system of the implantable defibrillator and are delivered through a pair of defibrillator electrodes. The pulses 42 are typically on the order of 15 volts but may be as low as 9 volts. The pulse width for each pulse is preferably 1.1 milliseconds with the delay between successive pulses that can range from 30 to 50 milliseconds. Unlike the overdrive pacing technique, all of the pulses 42 of the pulse train have the same pulse width. An example of this type of pulse-train, fibrillation-inducing waveform 40 is shown in European Patent Application EP 0 589 252 82. While pulse-train fibrillation-inducing waveform 40 has the advantage of more consistent induction of fibrillation than the overdrive pacing technique or the shock into the T-wave technique, the characteristic nature of the fibrillation induced using the pulse-train waveform 40 is a coarser fibrillation in that there is still a relatively high degree of coordination and organization of the electrical wavefronts in the heart.

Both the shock into the T-wave fibrillation-inducing waveform 30 and the pulse-train fibrillation-inducing waveform 40 have an advantage over the overdrive pacing fibrillation-inducing waveform 20 in that inducing fibrillation using the defibrillation electrodes, rather than the pacing electrodes, provides for a more conservative and accurate test of the capacity of the implantable defibrillator. Unfortunately, none of these three techniques for generating fibrillation-inducing waveforms using an implantable defibrillator is as reliable or effective as the fibrillation-inducing waveform 10 which is preferred for transthoracic implantation procedures. While the application of an alternating current directly to the defibrillation of electrodes of several seconds, is known to be an extremely reliable method for inducing fibrillation, as has been pointed out in several of the patents related to the prior art techniques, it has generally been assumed that this approach of using an AC current required external equipment or the addition of significant additional circuitry to an existing implantable defibrillator.

Figure 6:
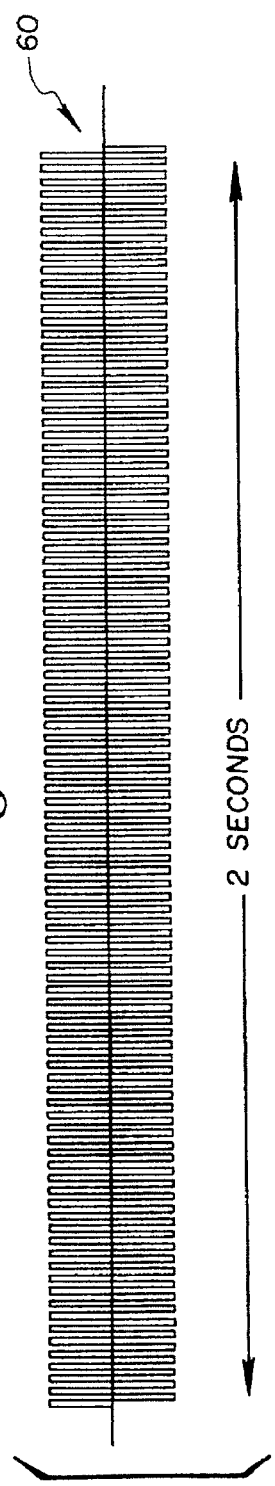
FIG. 6 shows an alternating current (AC) embodiment of a continuous fibrillation waveform in accordance with the present invention.
Figure 5:
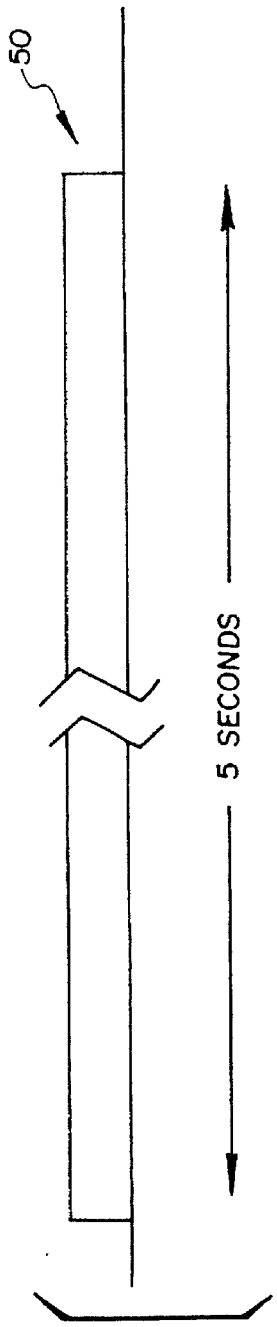
FIG. 5 shows a direct current (DC) embodiment of a continuous fibrillation waveform in accordance with the present invention.

Referring now to FIG. 5, a first embodiment of a continuous fibrillation-inducing waveform 50 in accordance with the present invention is shown. In this embodiment, a long duration direct current (DC) square wave having a voltage of, for example, 10 volts, is continuously applied to the defibrillation electrodes for a period of five seconds. FIG. 6 shows an alternating current (AC) embodiment of a continuous fibrillation-inducing waveform 60 in accordance with the present invention. This embodiment, an alternating square wave oscillates between peak-to-peak voltages of +20 volts and −20 volts. The frequency of the square wave is 20 milliseconds, for example, which corresponds to a frequency of 50 hertz or 50 cycles per second. Both fibrillation-inducing waveforms 50 and 60 more closely resemble the characteristics of 60 Hertz fibrillation-inducing waveform 10 and, accordingly, have been found to be much more reliable and effective for inducing the type of fine fibrillation in the patient's heart which provides the best test conditions for determining the defibrillation threshold (DFT) for an implantable defibrillator.

None of the existing techniques for generating fibrillation-inducing waveforms 20, 30 or 40 are capable of generating the fibrillation-inducing waveforms 50 and 60 of the present invention. The typical pacing circuitry associated with overdrive pacing fibrillation-inducing waveform 20 is capable of generating a series of short pacing volts typically six volts or less and simply does not have the capacity required for the energy associated with continuous fibrillation-inducing waveforms 50 and 60. On the other hand, the defibrillation circuitry of the implantable defibrillator can easily generate the energy required for such fibrillation-inducing waveforms 50 and 60, but it is typically designed to produce relatively short, discrete high voltage capacitive discharge pulses. Conventional wisdom has assumed that significant additional circuitry would be required in order to use the defibrillation circuitry to generate an AC 60 Hertz fibrillation-inducing waveform 10 within an implantable defibrillator.

Figure 7:
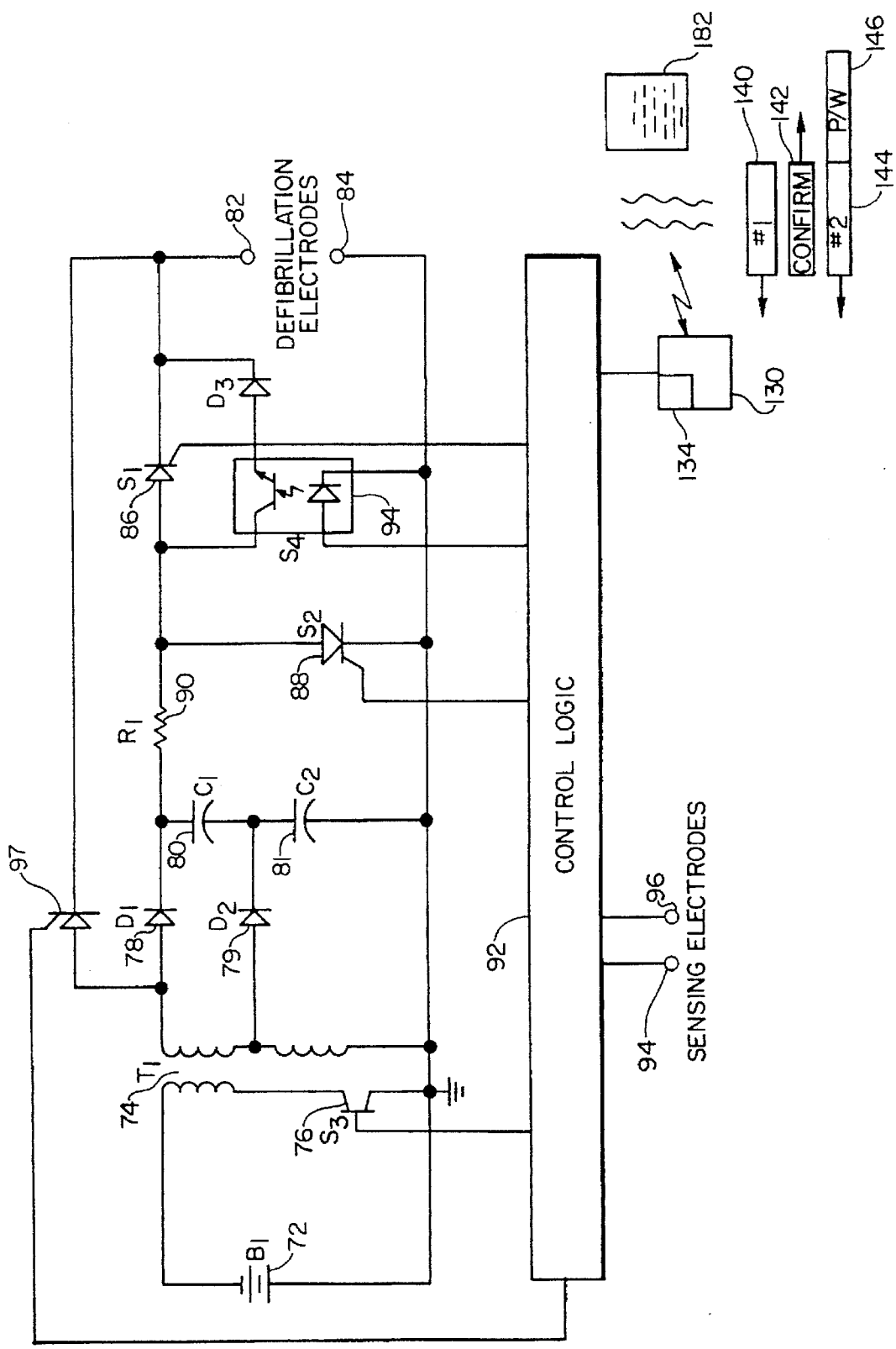
FIG. 7 is a simplified schematic diagram of the circuitry of an implantable defibrillator in accordance with the present invention.

In contrast to the conventional wisdom concerning the generation of fibrillation-inducing waveforms, the present invention recognizes that effective fibrillation-inducing waveforms 50 and 60 having voltage outputs of no more than 50 volts can be generated with little modification to the existing circuitry of an implantable defibrillator by operating the defibrillation charging circuitry in an unconventional manner. To understand how the present invention can use the charging circuitry of an existing implantable defibrillator to generate fibrillation-inducing waveforms 50 and 60, it is necessary to understand the operation of that circuitry. Referring now to FIG. 7, a schematic diagram of a conventional monophasic implantable defibrillator 70 is shown. Battery system 72 generates a primary current through transformer 74 which is interrupted at a high frequency by transistor switch 76. The high voltage output of transformer 74 is captured through diodes 78, 79 and capacitors 80, 81 which are then eventually charged, in series, to the desired defibrillation shock voltage. At the time that a countershock is to be delivered to defibrillation electrodes 82, 84, silicon controlled rectifier (SCR) switch 86 is turned on. This delivers the charge stored in capacitors 80, 81 to the heart through defibrillation electrodes 82, 84. At the time that the defibrillation countershock is truncated, SCR switch 88 is turned on. This rapidly discharges capacitors 80, 81 through a small resistor 90. As a result, SCR switch 86 is back biased which brings the countershock pulse being delivered to the heart to an end. The operation of transistor switch 76 and SCR switches 86 and 88 is controlled by control logic 92, which is preferably a programmable microprocessor or microcontroller, but alternatively could be implemented using a discrete logic components. The charging system, consisting of battery 72, transformer 74, transistor switch 76 are capable of delivering several watts of power to capacitors 80, 81 during the charging of the capacitors. The power transfer through the charging system can be represented by Eq.(1) as follows:

$$P = \text{energy/charge time} \qquad \text{Eq.(1)}$$

In a typical situation where capacitors 80, 81 need to be charged to a typical defibrillation energy of 30 joules in a charge time of, for example, 15 seconds, the requisite power transfer of the charging system as defined by Eq. (1) is given by:

$$P = 30 \text{ J}/15 \text{ s} = 2 \text{ watts}. \qquad \text{Eq.(2)}$$

Thus, a typical ICD charging system is capable of transferring energy at a rate of at least 2 watts into the charge storage capacitors 80, 81. Those capacitors are maintained at a steady voltage while they are being connected to defibrillation electrodes 82, 84 a voltage (V) would be generated across the defibrillation electrode resistance (R). These parameters would relate to the power transfer of the implantable defibrillator according to the terms of Eq. (3) as follows:

$$P=V/R \qquad \text{Eq.(3)}$$

Typical values for the inter-electrode resistance across a pair of defibrillation electrodes are 50 ohms. Rearranging Eq.(3) to solve for the voltage developed across the defibrillation electrodes yields as follows:

$$V=\sqrt{PR}=\sqrt{(2)(50)}=10 \qquad \text{Eq.(4)}$$

Thus, if charging circuitry of an implantable defibrillator is continuously operated while the capacitors 80, 81 are selectively connected to the defibrillation electrodes 82, 84, a voltage of at least 10 volts is developed across the defibrillation electrodes. In reality, this voltage is actually somewhat higher due to the fact that at very low voltages the inter-electrode resistance is inversely proportional to the voltage due to the non-linear electrical chemical effects which are exhibited near the defibrillation electrodes. A typical relationship is shown in Eq.(5) as follows:

$$R=1500/V \qquad \text{Eq.(5)}$$

Combining equations 5 and 4 to solve for V gives us:

$$V=\sqrt[3]{V(P)(1500)}=\sqrt[3]{3000}=14.45 \qquad \text{Eq.(6)}$$

In this example, it will be seen that, if fibrillation-inducing waveform 50 is applied for a period of one second in order to induce fibrillation, the total energy drain on battery system 72 is essentially equivalent to delivery of one defibrillation countershock. Thus, in a typical situation where no more than three to four fibrillations are induced during the process of establishing a DFT for an implantable defibrillator, the total energy consumed from battery system 72 will be no more than 100 joules, or less than the equivalent of three to four defibrillation countershocks. For most implantable defibrillator systems, this amount of energy is well within the extra storage capacity of battery system 72 so as to justify the use of the battery system 72 as means for inducing fibrillation.

To induce fibrillation using this circuitry, the capacitors 80, 81 are charged for a fraction of a second. At this point SCR switch 86 is turned on to begin transferring the power from the charging circuit through capacitors 80, 81 into defibrillation electrodes 82, 84. It will be seen that it is beneficial to delay a fraction of a second after initiating charging capacitors 80, 81 before turning on SCR switch 86 as SCR switch 86 will not stay turned on without a minimum "holding current". With transformer 74 running continuously, the voltage across the series combination of capacitors 80, 81 will stabilize at some value around 10 to 20 volts, depending upon the electrode impedance and the power capabilities of the charging circuitry. This steady DC voltage will induce fibrillation in the patient's heart after only a couple of seconds. Thus, by operating transformer 74 in a continuous manner under the control of control logic 92, the conventional circuitry for an implantable defibrillator as shown in FIG. 7 can achieve the fibrillation waveform of FIG. 5. Control logic 92 may be optionally connected to sensing electrodes 94, 96 for sensing an electrical activity of the heart, and, in response to a fibrillation pattern of a predetermined quality for a given period of time, terminating the fibrillation waveform. Switch 98 may be used to selectively directly connect transformer 74 with defibrillation electrodes 82, 84.

Figure 8:
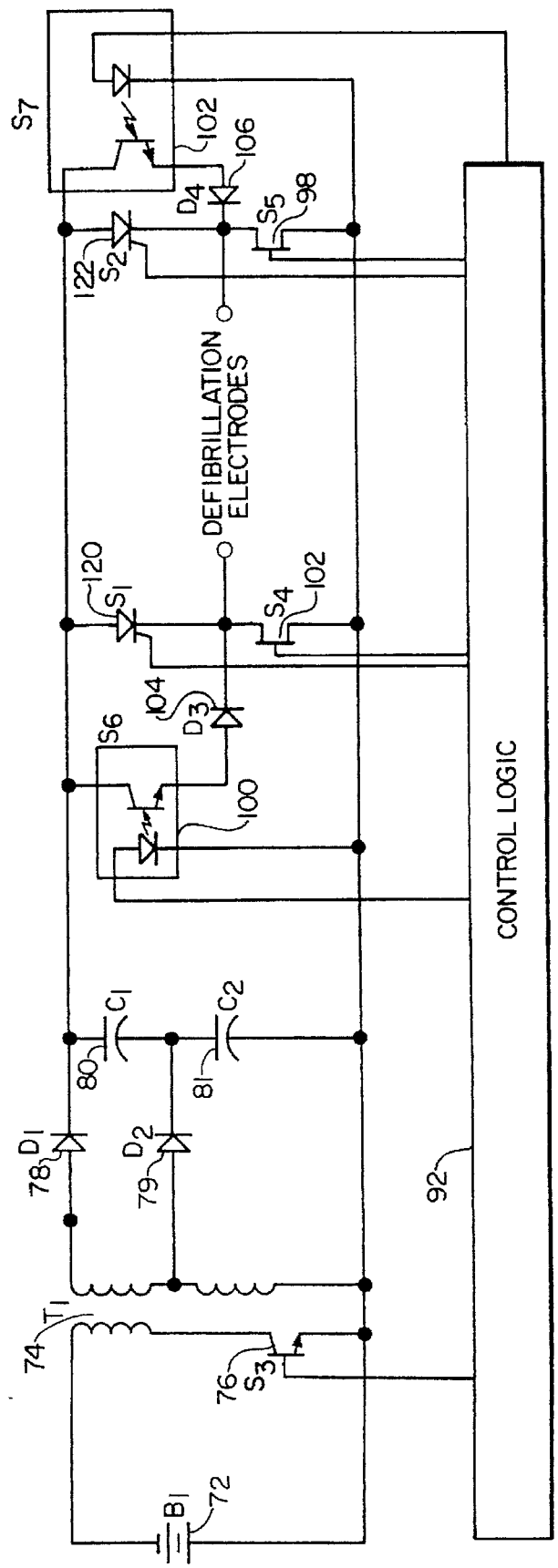
FIG. 8 is a schematic diagram of an alternate embodiment of the circuitry of the implantable defibrillator in accordance with the present invention.

With some minor modifications, more sophisticated fibrillation inducing waveforms can be generated. Referring to FIG. 8, a circuit for generating a fibrillation-inducing waveform as shown in FIG. 6, will now be described. In FIG. 8, the implantable defibrillator as similar components and operation to the implantable defibrillator described with respect to FIG. 7 in addition, a pair of optically coupled switches 100, 102 and associated protection diodes 104, 106 are added to a conventional H-bridge circuitry for the generation of a biphasic waveform. Operation of this circuit is essentially similar to that discussed earlier with respect to FIG. 7, except that FET switch 98 (field effector transistor) would also need to be turned on in order to complete the circuit to generate the DC defibrillation voltage shown in FIG. 5. An alternative operation of the circuitry shown in FIG. 8, would involve the use of the H-bridge 100 in order to generate an AC (alternating current) square wave as shown in FIG. 6. Again, the capacitors 80, 81 would be continuously charged by operation of the charging circuitry. SCR switch 122 and FET switch 102 would be turned on, for example, 10 milliseconds. FET switch 102 would then be turned off which would automatically turn off SCR switch 122 due to the fact that is was starved out of its holding current. Shortly thereafter SCR switch 122 and FET switch 98 would be turned on to deliver an approximately 10 to 20 volt signal in the reverse polarity to defibrillation electrodes 82, 84. This cycle would then be continued for a couple of seconds at a duty cycle anywhere on the order of 30 Hertz to 100 Hertz. Another alternative approach would be to use optically coupled switches 100, 102 along with their protection diodes 104, 106. This would obviate the need to turn on SCR switches 120, 122. Optically coupled transistor switch 110 could be used in lieu of SCR switch 86 and optically coupled transistor switch 112 could be used in lieu of SCR switch 88. By their alternate action they would alternating current format for fibrillation as shown in FIG. 6.

In an alternate embodiment of the present invention, a charge pump circuit may be used to increase the voltage output of battery system 72 by a factor of two to four times if higher output voltages are desired.

In a preferred embodiment, fibrillation inducing waveform 60 is delivered from an right ventricular defibrillation to a CAN electrode, and can consistently induce fibrillation at least 99% of the time by having a peak voltage of at least 10 volts applied for a duration of at least 2 seconds. In this example, fibrillation can be consistently induced 100% of the time if the duration is extended to about 3 seconds. FIG. 9 shows a graphic representation of the preferred ranges of peak voltages and durations of fibrillation inducing waveforms 50, 60. The shaded area 200 represents values for which consistent induction of fibrillation can be guaranteed using fibrillation-inducing waveforms 50, 60. It can be seen that for durations under 1 second, the voltage required to induce fibrillation are more than 20 V and it has been found that the consistency with which fibrillation is induced decreases dramatically, even with higher voltages. In contrast, for durations longer than 5 seconds, tissue damage to the myocardium can result and, as a result, these values are not generally used. Within this range of durations, it has been found that peak voltage levels of between 5 and 20 volts will consistently induce fibrillation. Obviously, the exact minimum voltage required to induce fibrillation in a given patient will vary from patient to patient and will be affected by parameters such as electrode placement. In general, however, it has been found that fibrillation inducing waveforms can be generated by the ICD within this range and provide consistent results.

Generally, a fibrillation inducing waveform 50, 60 would be delivered by the ICD only during the initial implantation of the ICD. It is possible, however, that a physician may want to adjust certain therapeutic parameters or run additional test on a patient after the ICD has been implanted. As a security measure, it is possible to provide the ICD with a remote telemetry communication system 130 that will communicate with an external programmer 132 for the purpose of setting programmable values stored within the control circuitry 92 of the ICD, as shown in FIG. 7. In the case where post-implantation induction of fibrillation is desired under the control of an attending physician, a preferred embodiment of the ICD requires that a unique personal identification number (PIN) be provided from the external programmer 132 to the communication system 130. This PIN is then verified against a value stored in non-volitale memory 134 within the ICD to confirm that, what could otherwise be a life-threatening condition, is authorized.

In a preferred embodiment, the telemetry system 130 would receiving a first command 140 from an external programmer 132 to initiate a fibrillation waveform; and would require that a second, confirmation command 144 from the external programmer 132 be received before the fibrillation is activated. Preferably, at least a portion of the second, confirmation command 144 includes a code 146 unique to the particular implantable defibrillator device. As an added precaution, when the command is received by the telemetry system 130 from the external programmer 132, the telemetry system 130 transmits a confirmation request 142 to the external programmer 132 before the second, confirmation command 144 is received from the external source before the fibrillation is activated. Preferably, at least a portion of the second, confirmation command 144 is generated by the external programmer in response to the confirmation request.

We claim:

1. A method of operating an implantable defibrillator device to induce fibrillation in a heart of a human patient, the implantable defibrillator device comprising at least two human implantable electrodes and a self-contained human implantable housing containing a battery system, a transformer system, a capacitor system and a sensing system for sensing cardiac electrical activity, all of which are connected to and controlled by a control system, the method comprising the device-implemented steps of:
   (a) receiving a command in the control system to generate a fibrillation waveform for the purpose of testing the implantable defibrillator device; and
   (b) operating the control system to cause the battery system, the transformer or the capacitor system to generate a continuous fibrillation waveform having a voltage of at least 5 volts and not more than 50 volts and a duration of not less than 500 milliseconds to be applied though the at least two implantable electrodes so as to induce fibrillation in the heart of the human patient.

2. The method of claim 1 wherein the fibrillation waveform of step (b) is a continuous DC waveform generated by a discharge of the capacitor system or the battery system.

3. The method of claim 1 wherein the device further includes output inverting circuitry connected to the control system and wherein step (b) further comprises the step of utilizing the output inverting circuitry to periodically invert a polarity of the continuous fibrillation waveform to generate an AC waveform having a peak-to-peak voltage output ranging from at least 10 volts to no more than 100 volts.

4. The method of claim 3 wherein the step of periodically inverting the polarity controls a duty cycle of the AC waveform so as to generate a frequency between 30 hertz and 100 hertz.

5. The method of claim 1 wherein step (b) causes the continuous fibrillation waveform to have a voltage of more than 10 volts and less than 25 volts.

6. The method of claim 1 wherein step (b) causes the duration of the continuous fibrillation waveform to be longer than one second.

7. The method of claim 1 wherein step (b) is accomplished by continuously operating the transformer system to charge the capacitor during the duration of the fibrillation waveform.

8. The method of claim 1 wherein step (b) is accomplished by selectively connecting the transformer system directly to the at least two implantable electrodes.

9. The method of claim 8 wherein step (b) further includes the step of continuously operating the transformer system during the duration of the fibrillation waveform.

10. The method of claim 8 wherein step (b) further includes the step of cycling the transformer system at a duty cycle less than 100 percent during the duration of the fibrillation waveform.

11. The method of claim 1 wherein step (b) is accomplished by:
   (b1) initially charging the capacitor system to a charging voltage of not more than 50 volts; and
   (b2) cycling the transformer system at a duty cycle of less than 100 percent to recharge the capacitor system during a continuous discharge of the capacitor system through the at least two implantable electrodes.

12. The method of claim 1 wherein step (b) is accomplished by:
   (b1) selectively connecting the battery system directly to at least two implantable defibrillation electrodes; and
   (b2) discharging the battery system through the at least two defibrillation electrodes to generate the continuous fibrillation waveform.

13. The method of claim 1 wherein the device further includes a voltage multiplier circuit and wherein step (b) is accomplished by:
   (b1) increasing a voltage output of the battery system by connecting the battery system to the voltage multiplier circuit;
   (b2) selectively connecting a voltage output of the voltage multiplier circuit to the at least two implantable electrodes; and
   (b3) discharging the battery system through the voltage multiplier circuit and the at least two implantable electrodes to generate the continuous fibrillation waveform.

14. The method of claim 1 further comprising a transmission source external to the human patient wherein step (a) comprises the steps of:
   (a1) receiving a first command from the external transmission source to initiate a fibrillation waveform; and
   (a2) receiving a second, confirmation command from the external transmission source before initiating step (b).

15. The method of claim 14 wherein at least a portion of the second, confirmation command that is received in step (a2) includes a code unique to the particular implantable defibrillator device.

16. The method of claim 14 wherein step (a1) further comprises the step of:

(a1a) transmitting a confirmation request to the external transmission source.

17. The method of claim 16 wherein at least a portion of the second, confirmation command of step (a2) is generated by the external transmission source in response to the confirmation request.

18. The method of claim 1 further comprising the steps of:

(c) utilizing the sensing system to sense an electrical activity of the heart during step (b); and (d) utilizing the control system to compare the electrical activity sensed by step (c) to a fibrillation pattern of a predetermined quality and terminating step (b) when the electrical activity sensed by step (c) presents the fibrillation pattern of for at least a given period of time.

19. An implantable defibrillator device for inducing fibrillation in a human patient for the purpose of testing the device, the implantable defibrillator device comprising:

at least two human implantable electrodes; and a self-contained human implantable housing containing:

a battery system having a low voltage output of less than 20 volts;

a transformer system having a primary winding electrically connected to the low voltage output of the battery system and having a secondary winding that produces a high voltage output of at least 50 volts;

a capacitor system electrically connected to the high voltage output of the transformer system; and control means for controlling operation of the device, including:

defibrillation means for selectively controlling delivery of a high voltage defibrillation countershock from the capacitor system to the implantable electrodes; and fibrillation means for selectively controlling delivery of a continuous fibrillation waveform to the implantable electrodes, the fibrillation waveform having a voltage of at least 5 volts and not more than 50 volts and a duration of not less than 500 milliseconds.

20. The device of claim 19 wherein the fibrillation means comprises:

a switch electrically connected between the low voltage output of the battery system and the primary winding of the transformer system;

output switching circuitry electrically connected to the implantable electrodes; and controller means electrically connected to the switch and the output switching circuitry for enabling the transformer system to operate continuously during delivery of the continuous defibrillation waveform and for selectively connecting the high voltage output of the capacitor system to the implantable electrodes.

21. The device of claim 19 wherein the fibrillation means further comprises:

means for periodically inverting a polarity of the continuous fibrillation waveform to generate an AC waveform having a peak-to-peak voltage output ranging from at least 10 volts to no more than 100 volts.

22. The device of claim 21 wherein the controller means operates the switch to cycle the transformer system at a duty cycle less than 100 percent during the duration of the fibrillation waveform.

23. The device of claim 19 wherein the fibrillation means includes means for selectively connecting the secondary winding of the transformer system directly to the at least two implantable electrodes.

24. The device of claim 19 wherein the fibrillation means comprises:

switch means for selectively electrically connecting the low voltage output of the battery system directly to at least two defibrillation implantable electrodes; and controller means for discharging the battery system through the at least two defibrillation electrodes to generate the continuous fibrillation waveform.

25. The device of claim 19 further comprising a voltage multiplier circuit electrically connected to the low voltage output of the battery system and wherein the fibrillation means comprises:

switch means for selectively connecting a voltage output of the voltage multiplier circuit to the at least two implantable electrodes; and controller means for discharging the battery system through the voltage multiplier circuit and the at least two implantable electrodes to generate the continuous fibrillation waveform.

26. The device of claim 19 wherein the control means further comprises telemetry means for receiving a command from a transmission source external to the human patient to generate the fibrillation waveform.

27. The device of claim 26 wherein the telemetry means includes:

means for receiving a first command from the external transmission source to initiate a fibrillation waveform; and means for receiving a second, confirmation command from the external transmission source before the fibrillation means is activated.

28. The device of claim 27 wherein the command is received from an external transmission source and wherein the telemetry means further includes:

means for transmitting a confirmation request to the external transmission source and means for receiving a second, confirmation command from the external transmission source before the fibrillation means is activated.

29. The device of claim 19 wherein the control means further comprises means for sensing an electrical activity of the heart and comparing the electrical activity of the heart to a fibrillation pattern of a predetermined quality and wherein the fibrillation means further includes means for terminating the fibrillation waveform when the electrical activity matches the fibrillation pattern for at least a given period of time.

* * * * *